United States Patent [19]
Terranova et al.

[11] Patent Number: 6,099,593
[45] Date of Patent: *Aug. 8, 2000

[54] COMPOSITIONS FOR DYEING KERATIN FIBERS CONTAINING PYRAZOLO(1,5-A) PYRIMIDINE DERIVATIVES AND DYEING PROCESSES

[75] Inventors: Eric Terranova, Asnieres; Aziz Fadli, Le Blanc Mesnil; Alain Lagrange, Coupvray, all of France

[73] Assignee: L'Oreal, France

[*] Notice: This patent issued on a continued prosecution application filed under 37 CFR 1.53(d), and is subject to the twenty year patent term provisions of 35 U.S.C. 154(a)(2).

[21] Appl. No.: 08/981,589

[22] PCT Filed: Jun. 12, 1997

[86] PCT No.: PCT/FR97/01057

§ 371 Date: Dec. 31, 1997

§ 102(e) Date: Dec. 31, 1997

[87] PCT Pub. No.: WO97/49378

PCT Pub. Date: Dec. 31, 1997

[30] Foreign Application Priority Data

Jun. 21, 1996 [FR] France .................. 96 07776

[51] Int. Cl.⁷ ............................................. A61K 7/13
[52] U.S. Cl. ................... 8/409; 8/407; 8/423; 8/567; 8/573
[58] Field of Search ................ 8/406, 407, 408, 8/409, 423, 567, 573; 544/281; 548/360.5

[56] References Cited

U.S. PATENT DOCUMENTS

| 2,566,658 | 9/1951 | Fry | 544/281 |
| 3,626,064 | 12/1971 | Hitchings et al. | 514/258 |
| 5,234,818 | 8/1993 | Zimmermann et al. | 544/281 |
| 5,356,897 | 10/1994 | Oku et al. | 544/281 |
| 5,380,340 | 1/1995 | Neunhoeffer et al. | 8/409 |
| 5,457,200 | 10/1995 | Zimmermann et al. | 544/281 |

FOREIGN PATENT DOCUMENTS

| 0 433 854 | 6/1991 | European Pat. Off. . |
| 4029324 | 3/1992 | Germany . |

OTHER PUBLICATIONS

Chemical Abstracts, vol. 67, No. 3, Jul. 17, 1967, Abstract No. 11498c.

William E. Kirkpatrick et al., "3–Halo–5,7–dimethylpyrazolo[1,2–a]pyrimidines, a Nonbenzodiazepinoid Class of Antianxiety Agents Devoid of Potentiation of Central Nervous System Depressant Effects of Ethanol or Barbiturates", Journal of Medicinal Chemistry, vol. 20, No. 3, 1977, pp. 386–393.

*Primary Examiner*—Caroline D. Liott
*Attorney, Agent, or Firm*—Finnegan, Henderson, Farabow, Garrett & Dunner

[57] ABSTRACT

Novel compositions for the oxidation dyeing of keratin fibres, comprising at least one specific pyrazolo[1,5-a] pyrimidine derivative, a dyeing process using these compositions, novel pyrazolo[1,5-a]pyrimidine derivatives and a process for their preparation.

26 Claims, No Drawings

COMPOSITIONS FOR DYEING KERATIN FIBERS CONTAINING PYRAZOLO(1,5-A) PYRIMIDINE DERIVATIVES AND DYEING PROCESSES

The invention relates to novel compositions for the oxidation dyeing of keratin fibres, comprising at least one pyrazolo[1,5-a]pyrimidine derivative as oxidation base, to the dyeing process using this composition, to novel pyrazolo[1,5-a]pyrimidine derivatives and to a process for their preparation.

It is known to dye keratin fibres, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. Oxidation dye precursors, or oxidation bases, are colourless or weakly-coloured compounds which, when combined with oxidizing products, can give rise to coloured and dyeing compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of compounds used as regards the oxidation bases and the couplers allows a wide range of colours to be obtained.

The so-called "permanent" coloration obtained by means of these oxidation dyes must moreover satisfy a certain number of requirements. Thus, it must have no toxicological drawbacks, it must be able to give shades of the desired intensity and it must be able to withstand external agents (light, bad weather, washing, permanent waving, perspiration, rubbing).

The dyes must also be able to cover grey hair and, lastly, they must be as unselective as possible, that is to say that they must make it possible to obtain the smallest possible colour differences along the entire length of the same keratin fibre, which may, in fact, be differently sensitized (i.e. damaged) between its tip and its root. They must also have good chemical stability in the formulations. They must have a good toxicological profile.

It has already been proposed, in particular in patent application DE 4,029,324, to use certain pyrazolo[1,5-a]pyrimidine derivatives which can be substituted with $C_1$–$C_4$ alkyl radicals in position 4, 5 and/or 6, as couplers for the oxidation dyeing of keratin fibres.

It has also been proposed in patent application DE 4,133,957 to use certain pyrazolo[1,5-a]pyrimidine derivatives belonging to the tetrahydropyrazolo[1,5-a]pyrimidine family as oxidation dye precursors for the oxidation dyeing of keratin fibres.

The Applicant has just discovered, entirely unexpectedly and surprisingly, a novel family of pyrazolo[1,5-a]pyrimidine derivatives of formula (I) defined below, which are partly novel per se, these derivatives possibly being suitable for use as oxidation dye precursors, but in addition making it possible to obtain dye compositions which lead to intense colorations and which have good resistance to external agents (light, bad weather, washing, permanent waving, perspiration and rubbing). Lastly, these compounds prove to be readily synthesizable and are chemically stable. They have a good toxicological profile.

These discoveries form the basis of the present invention.

A first subject of the invention is thus a composition for the oxidation dyeing of keratin fibres, and in particular human keratin fibres such as the hair, characterized in that it comprises, in a medium which is suitable for dyeing, at least one pyrazolo[1,5-a]pyrimidine derivative of formula (I) below as oxidation base and/or one of the addition salts thereof with an acid or with a base and/or one of the tautomeric forms thereof, when a tautomeric equilibrium exists:

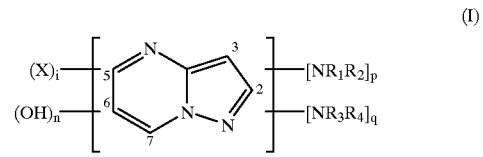

(I)

in which:

$R_1$, $R_2$, $R_3$ and $R_4$, which may be identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a ($C_1$–$C_4$)alkoxy($C_1$–$C_4$)alkyl radical, a $C_1$–$C_4$ aminoalkyl radical (it being possible for the amine to be protected with an acetyl, an amido or a sulphonyl), a ($C_1$–$C_4$)alkylamino($C_1$–$C_4$)alkyl radical, a di[($C_1$–$C_4$)alkyl]amino($C_1$–$C_4$)alkyl radical (it being possible for the dialkyls to form a 5- or a 6-membered aliphatic or heterocyclic ring), or a hydroxy($C_1$–$C_4$)alkylamino($C_1$–$C_4$)alkyl or di[hydroxy($C_1$–$C_4$)alkyl]amino($C_1$–$C_4$)alkyl radical;

the radicals X, which may be identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$) alkylamino($C_1$–$C_4$)alkyl radical, a di[($C_1$–$C_4$)alkyl]amino($C_1$–$C_4$)alkyl radical (it being possible for the dialkyls to form a 5- or 6-membered aliphatic or heterocyclic ring), a hydroxy($C_1$–$C_4$)alkylamino($C_1$–$C_4$)alkyl radical, a di[hydroxy($C_1$–$C_4$)alkyl]amino($C_1$–$C_4$)alkyl radical, an amino radical, a ($C_1$–$C_4$) alkylamino radical or a di[($C_1$–$C_4$)alkyl]amino radical, a halogen atom, a carboxylic acid group or a sulphonic acid group;

i is equal to 0, 1, 2 or 3;

p is equal to 0 or 1;

q is equal to 0 or 1;

n is equal to 0 or 1;

with the proviso that:
  (i) the sum p+q is other than 0;
  (ii) when p+q is equal to 2, then n is equal to 0 and the groups $NR_1R_2$ and $NR_3R_4$ occupy positions (2,3); (5,6); (6,7); (3,5) or (3,7);
  (iii) when p+q is equal to 1, then n is equal to 1 and the group $NR_1R_2$ (or $NR_3R_4$) and the OH group occupy positions (2,3); (5,6); (6,7); (3,5) or (3,7).

When the compounds of formula I are such that they contain an OH group on one of the positions 2, 5 or 7 α to a nitrogen atom, a tautomeric equilibrium exists which is represented, for example, by the following scheme:

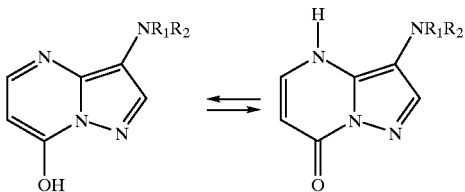

In general, the addition salts with an acid which can be used in the context of the dye compositions of the invention (oxidation bases and couplers) are chosen in particular from the hydrochlorides, hydrobromides, sulphates, tartrates, lactates and acetates. The addition salts with a base which can be used in the context of the dye compositions of the invention (oxidation bases and couplers) are, in particular, those obtained with sodium hydroxide, potassium hydroxide, aqueous ammonia or amines.

Among the pyrazolo[1,5-a]pyrimidine derivatives of formula (I) which can be used as oxidation bases in the compositions in accordance with the invention, mention may be made in particular of:

pyrazolo[1,5-a]pyrimidine-3,7-diamine;

2-methylpyrazolo[1,5-a]pyrimidine-3,7-diamine;

2,5-dimethylpyrazolo[1,5-a]pyrimidine-3,7-diamine;

pyrazolo[1,5-a]pyrimidine-3,5-diamine;

2,7-dimethylpyrazolo[1,5-a]pyrimidine-3,5-diamine;

3-aminopyrazolo[1,5-a]pyrimidin-7-ol;

3-amino-5-methylpyrazolo[1,5-a]pyrimidin-7-ol;

3-aminopyrazolo[1,5-a]pyrimidin-5-ol;

2-(3-aminopyrazolo[1,5-a]pyrimidin-7-ylamino)ethanol;

3-amino-7-β-hydroxyethylamino-5-methylpyrazolo[1,5-a]pyrimidine;

2-(7-aminopyrazolo[1,5-a]pyrimidin-3-ylamino)ethanol;

2-[(3-aminopyrazolo[1,5-a]pyrimidin-7-yl)(2-hydroxyethyl)amino]ethanol;

2-[(7-aminopyrazolo[1,5-a]pyrimidin-3-yl)(2-hydroxyethyl)amino]ethanol;

5,6-dimethylpyrazolo[1,5-a]pyrimidine-3,7-diamine;

2,6-dimethylpyrazolo[1,5-a]pyrimidine-3,7-diamine;

2,5-N-7,N-7-tetramethylpyrazolo[1,5-a]pyrimidine-3,7-diamine;

and the addition salts thereof and the tautomeric forms thereof, when a tautomeric equilibrium exists.

The pyrazolo[1,5-a]pyrimidine derivatives of the invention of formula (I) can be prepared according to known methods described in the literature. Reference may be made, for example, to the following references:

The pyrazolo[1,5-a]pyrimidine derivatives of the invention of formula (I) can be prepared by cyclization from an aminopyrazole according to the syntheses described in the following references:

EP 628559 BEIERSDORF-LILLY

R. Vishdu, H. Navedul, *Indian J. Chem.*, 34b (6), 514, 1995.

N. S. Ibrahim, K. U. Sadek, F. A. Abdel-Al, *Arch. Pharm.*, 320, 240, 1987.

R. H. Springer, M. B. Scholten, D. E. O'Brien, T. Novinson, J. P. Miller, R. K. Robins, *J. Med. Chem.*, 25, 235, 1982.

T. Novinson, R. K. Robins, T. R. Matthews, *J. Med. Chem.*, 20, 296, 1977.

US 3907799 ICN PHARMACEUTICALS

The pyrazolo[1,5-a]pyrimidine derivatives of formula (I) of the invention can be prepared by cyclization from hydrazine according to the syntheses described in the following references:

A. McKillop and R. J. Kobilecki, *Heterocycles*, 6(9), 1355, 1977.

E. Alcade, J. De Mendoza, J. M. Marcia-Marquina, C. Almera, J. Elguero, *J. Heterocyclic Chem.*, 11(3), 423, 1974.

K. Saito, I. Hori, M. Higarashi, H. Midorikawa, *Bull. Chem. Soc. Japan*, 47(2), 476, 1974.

By way of illustration, the 3-aminopyrazolo[1,5-a]pyrimidine derivatives of formula (I) of the invention can, for example, be prepared according to the process described in Scheme 1.

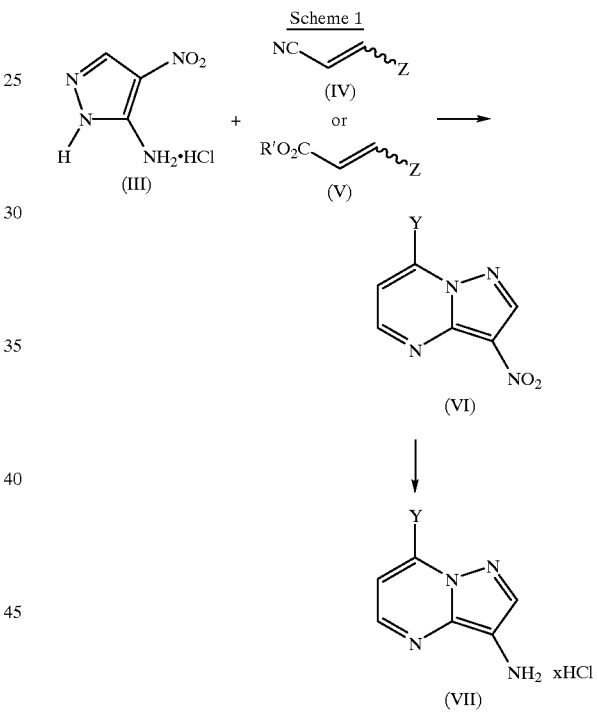

4-Nitro-2H-pyrazol-3-ylamine hydrochloride (III) (prepared according to H. Dorn and H. Dilcher, *Liebigs Ann. Chem.* 707, 141, 1967) can be cyclized in the presence of an acrylonitrile derivative (IV) (Z=MeO, EtO or $Me_2N$) or of an acrylate (V) (Z=MeO, EtO or $Me_2N$; R'=$C_1$–$C_4$ alkyl, aryl) in order to lead to the pyrazolo[1,5-a]pyrimidines of structure (VI) (Y=$NH_2$,OH). This reaction can be carried out based on the method of G. Mühmel, R. Hanke and E. Breitmaier described in *Synthesis*, 673, 1982. The list of derivatives which can be cyclized with 4-nitro-2H-pyrazol-3-ylamine (III) is not limited to the acrylonitrile and acrylate derivatives alone. Mention may be made, for example, of β-keto ester derivatives (VIII) (X has the same definition as for the groups X in formula (I) above; R'=$C_1$–$C_4$ alkyl, aryl), β-keto nitrile derivatives (IX) (X has the same definition as for the groups X in formula (I) above) or β-cyano acetal derivatives (X) (R'=$C_1$–$C_4$ alkyl) without being limiting.

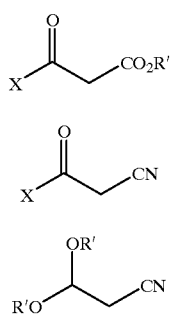

The pyrazolo[1,5-a]pyrimidines of structure (VI) can then be reduced according to known processes (R. Hemmer, W. Lürken, in Houben-Weyl, "Methoden der Organischen Chemie", vol. E16d, pp. 815 ff.). It will be preferred to use metals such as palladium (Pd), platinum (Pt) or nickel (Ni) in the presence of a hydrogen donor such as ammonium formate, formic acid or alternatively cyclohexene instead of hydrogen (S. Ram, R. E. Ehrenkaufer, *Synthesis*, 91, 1988). Metals such as zinc (Zn), tin (Sn) or iron (Fe) in an acidic medium such as aqueous hydrochloric acid or aqueous acetic acid may also be used, optionally with addition of an organic solvent such as methanol, ethanol or tetrahydrofuran.

The pyrazolo[1,5-a]pyrimidine derivative(s) of formula (I) above preferably represent from 0.0005 to 12% by weight approximately relative to the total weight of the dye composition, and even more preferably from 0.005 to 6% by weight approximately relative to this weight.

The medium which is suitable for dyeing (or the support) generally consists of water or of a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally approximately between 3 and 12, and preferably approximately between 5 and 11. It can be adjusted to the desired value using acidifying or basifying agents usually used for dyeing keratin fibres, or alternatively using standard buffer systems.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (II) below:

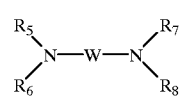

in which W is a propylene residue optionally substituted with a hydroxyl group or a $C_1$–$C_4$ alkyl radical; $R_5$, $R_6$, $R_7$ and $R_8$, which may be identical or different, represent a hydrogen atom or a $C_1$–$C_4$ alkyl or $C_1$–$C_4$ hydroxyalkyl radical.

In addition to the dyes defined above, the dye composition in accordance with the invention can also contain at least one additional oxidation base which can be chosen from the oxidation bases conventionally used in oxidation dyeing and among which mention may be made, in particular, of para-phenylenediamines, bis(phenyl)alkylenediamines, para-aminophenols, ortho-aminophenols and heterocyclic bases other than the pyrazolo[1,5-a]pyrimidine derivatives of formula (I) used in accordance with the invention.

Among the para-phenylenediamines, mention may be made more particularly, by way of example, of para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline and the para-phenylenediamines described in French patent application FR 2,630,438, and the addition salts thereof.

Among the bis(phenyl)alkylenediamines, mention may be made more particularly, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)-tetramethylenediamine, N,N'-bis(4-methylaminophenyl)-tetramethylenediamine and N,N'-bis(ethyl)-N,N'-bis(4'-amino-3'-methylphenyl) ethylenediamine, and the addition salts thereof.

Among the para-aminophenols, mention may be made more particularly, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof.

Among the ortho-aminophenols, mention may be made more particularly, by way of example, of 2-aminophenol, 2-amino-5-methylphenol, 2-amino-6-methylphenol and 5-acetamido-2-aminophenol and the addition salts thereof.

Among the heterocyclic bases, mention may be made more particularly, by way of example, of pyridine derivatives, pyrimidine derivatives and pyrazole derivatives other than the pyrazolo[1,5-a]pyrimidine derivatives of formula (I) used in accordance with the invention, and the addition salts thereof.

When they are used, these additional oxidation bases preferably represent from 0.0005 to 12% by weight approximately relative to the total weight of the dye composition, and even more preferably from 0.005 to 6% by weight approximately relative to this weight.

The oxidation dye compositions in accordance with the invention can also contain at least one coupler and/or at least one direct dye, in particular in order to modify the shades or to enrich them with glints.

The couplers which can be used in the oxidation dye compositions in accordance with the invention can be chosen from the couplers used conventionally in oxidation dyeing and among which mention may be made, in particular, of meta-phenylenediamines, meta-aminophenols, meta-diphenols and heterocyclic couplers such as, for example, indole derivatives, and the addition salts thereof.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethyl)amino-1-methoxybenzene, 1,3-diaminobenzene, 1,3-bis(2,4-diaminophenoxy)propane, 3-ureidoaniline, 3-ureido-1-dimethylaminobenzene, sesamol, α-naphthol, 6-hydroxyindole, 4-hydroxyindole and 4-hydroxy-N-methylindole and the addition salts thereof.

When they are present, these couplers preferably represent from 0.0001 to 10% by weight approximately relative to the total weight of the dye composition, and even more preferably from 0.005 to 5% by weight approximately relative to this weight.

The dye composition according to the invention can also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, film-forming agents, preserving agents and opacifiers.

Needless to say, a person skilled in the art will take care to select this(ese) optional additional compound(s) such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

A subject of the invention is also a process for dyeing keratin fibres, and in particular human keratin fibres such as the hair, using the dye composition as defined above.

According to this process, at least one dye composition as defined above is applied to the fibres for a period which is sufficient to develop the desired coloration, either in air or using an oxidizing agent. The dye composition can optionally contain oxidation catalysts in order to accelerate the oxidation process.

According to a first embodiment of the process of the invention, the fibres are coloured without the addition of an oxidizing agent, but merely by contact with atmospheric oxygen.

According to a second embodiment of the process of the invention, at least one dye composition as defined above is applied to the fibres, the colour being developed at acidic, neutral or alkaline pH using an oxidizing agent which is added, only at the time of use, to the dye composition or which is present in an oxidizing composition that is applied simultaneously or sequentially in a separate manner.

According to this second embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents used conventionally for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably ranges from 3 to 12 approximately, and even more preferably from 5 to 11. It is adjusted to the desired value using acidifying or basifying agents usually used for dyeing keratin fibres and as defined above.

The oxidizing composition as defined above can also contain various adjuvants used conventionally in compositions for dyeing the hair and as defined above.

The composition which is finally applied to the keratin fibres can be in various forms, such as in the form of liquids, creams or gels or in any other form which is suitable for dyeing keratin fibres, and in particular human hair.

Another subject of the invention is a multi-compartment dyeing "kit" or device or any other multi-compartment packaging system, a first compartment of which contains the dye composition as defined above and a second compartment of which contains the oxidizing composition as defined above. These devices can be equipped with means for allowing the desired mixture to be applied to the hair, such as the devices described in patent FR-2,586,913 in the name of the Applicant.

Certain compounds of formula (I), used as oxidation bases in the context of the present invention, are novel and, in this respect, constitute another subject of the invention.

These novel pyrazolo[1,5-a]pyrimidine derivatives, the addition salts thereof with an acid or a base and the tautomeric forms thereof, when a tautomeric equilibrium exists, correspond to formula (I') below:

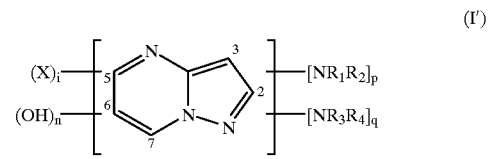

in which the radicals $R_1$, $R_2$, $R_3$, $R_4$, X, i, n, p and q have the same meanings as those indicated above in formula (I), except for the following compounds:

pyrazolo[1,5-a]pyrimidine-6,7-diamine;

5,6-dimethylpyrazolo[1,5-a]pyrimidine-3,7-diamine;

2,6-dimethylpyrazolo[1,5-a]pyrimidine-3,7-diamine;

2,5-N7, N7-tetramethylpyrazolo[1,5-a]pyrimidine-3,7-diamine;

2,3-dimethylpyrazolo[1,5-a]pyrimidine-6,7-diamine;

6-amino-5-methylpyrazolo[1,5-a]pyrimidin-7-ol;

2,5-dimethyl-6-phenyl[1,5-a]pyrimidine-3,7-diamine;

2,6-dimethyl-5-benzyl[1,5-a]pyrimidine-3,7-diamine; and the addition salts thereof.

Among the novel compounds of formula (I'), mention may be made in particular of:

pyrazolo[1,5-a]pyrimidine-3,7-diamine;
2-methylpyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-amino-5-methylpyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
3-amino-7-β-hydroxyethylamino-5-methylpyrazolo[1,5-a]pyrimidine;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;

as well as the addition salts thereof and the tautomeric forms thereof when a tautomeric equilibrium exists.

The pyrazolo[1,5]pyrimidine derivatives of formula (I) as well as the addition salts thereof and the tautomeric forms thereof as defined above, can also be used as oxidation bases in, and for the preparation of, compositions intended for photography or chemical imaging.

The examples which follow are intended to illustrate the invention without, however, limiting its scope.

EXAMPLE 1

PYRAZOLO[1,5-a]PYRIMIDINE-3,7-DIAMINE DIHYDROCHLORIDE
1st step: 3-NITROPYRAZOLO[1,5-a]PYRIMIDIN-7-YLAMINE HYDROCHLORIDE

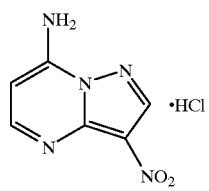

50 g of 4-nitro-2H-pyrazole-3-ylamine hydrochloride (prepared according to H. Dorn and H. Dilcher, Liebigs Ann. Chem., 707, 141, 1967) 35 g of β-ethoxyacrylonitrile and 250 cc of acetic acid were introduced into a 500 cc three-necked round-bottomed flask fitted with a mechanical stirrer and equipped with a condenser and a thermometer. The medium was refluxed for 4h30'. The mixture was cooled to about 40° C. and the precipitate was then filtered off. This precipitate was taken up in 300 cc of ethyl ether with stirring. The precipitate was filtered off again, washed on the filter with 100 cc of ethyl ether and the product was dried under vacuum over phosphorus pentoxide. 61.3 g of 3-nitropyrazolo[1,5-a]pyrimidin-7-ylamine hydrochloride were obtained in the form of a yellow powder. (Yield=93%).

NMR (DMSO-$d_6$): 6.70 (d; 1H); 8.34 (d; 1H); 8.99; (s; 1H); 9.56 (s; $NH_2$); 11.96 (S; $NH^+$);

ELEMENTAL ANALYSIS: $C_6H_5N_5O_2$•HCl MW=215.6

|  | C | H | N |
|---|---|---|---|
| Calculated (%) | 33.43 | 2.81 | 32.48 |
| Found (%) | 34.09 | 2.89 | 32.53 |

2nd step: PYRAZOLO[1,5-a]PYRIMIDINE-3,7-DIAMINE DIHYDROCHLORIDE

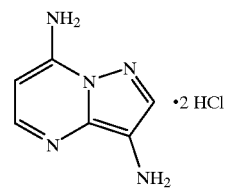

30 g of 3-nitropyrazolo[1,5-a]pyrimidin-7-ylamine hydrochloride, 7 g of 10% palladium-on-charcoal, 85 g of cyclohexene and 600 cc of acetic acid were introduced into a 1000 cc 3-necked round-bottomed flask fitted with a magnetic stirrer and equipped with a condenser and a thermometer. The medium was refluxed for 4h30' and the catalyst was then filtered off through Celite. This catalyst impregnated with product was taken up in 500 cc of refluxing water and was again filtered off. The two filtrates were combined and evaporated. 40 g of beige powder were obtained. This solid was taken up in 55 cc of concentrated hydrochloric acid and refluxed for 3 h. The product was filtered off at 15° C. and dried under vacuum over phosphorus pentoxide. 25 g of an off-white powder were obtained, which product was recrystallized from 80 cc of concentrated hydrochloric acid. 18 g of pyrazolo[1,5-a]pyrimidine-3,7-diamine dihydrochloride were collected in the form of a white powder. (Yield=60%).

NMR (DMSO-$d_6$): 6.45 (d; 1H); 8.36 (d; 1H); 8.39; (s; 1H); 8.60–11.50 (6H);

ELEMENTAL ANALYSIS: $C_6H_7N_5$•2 HCl.0.5 $H_2O$ MW=231

|  | C | H | N |
|---|---|---|---|
| Calculated (%) | 31.15 | 4.32 | 30.29 |
| Found (%) | 31.12 | 4.29 | 30.34 |

EXAMPLE 2
3-AMINOPYRAZOLO[1,5-a]PYRIMIDIN-7-OL HYDROCHLORIDE
1st step: 3-NITROPYRAZOLO[1,5-a]PYRIMIDIN-7-OL

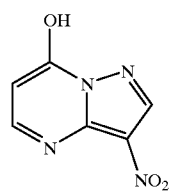

2 g of 4-nitro-2H-pyrazol-3-ylamine hydrochloride (prepared according to H. Dorn and H. Dilcher, Liebigs Ann. Chem., 707, 141, 1967), 1.55 g of methyl 3-methoxyacrylate and 20 cc of absolute ethanol were introduced into a 50 cc three-necked round-bottomed flask fitted with a magnetic stirrer and equipped with a condenser and a thermometer. The medium was refluxed for 5 h and the precipitate was then filtered off while hot. 1.2 g of a yellow solid were obtained. After chromatography on silica gel (Merck: 230–400 mesh; EcOAc/MeOH=9/1), 0.4 g of 3-nitropyrazolo[1,5-a]pyrimidin-7-ol was collected in the form of a yellow powder. (Yield=18%).

NMR (DMSO-$d_6$): 6.19 (d; 1H); 7.98 (d; 1H); 8.75 (s; 1H); 13.10 (OH).

2nd step: 3-AMINOPYRAZOLO[1,5-a]PYRIMIDIN-7-OL HYDROCHLORIDE

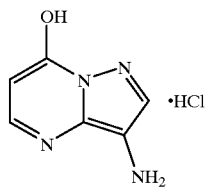

0.35 g of 3-nitropyrazolo[1,5-a]pyrimidin-7-ol, 20 cc of acetic acid, 1.6 g of cyclohexene and 85 mg of 10% palladium-on-charcoal were introduced into a 50 cc 3-necked round-bottomed flask fitted with a magnetic stirrer and equipped with a condenser and a thermometer. The medium was refluxed for 1h30' and the catalyst was then filtered off through Celite. After evaporation of the acetic acid, the solid obtained was taken up in 2 cc of refluxing concentrated hydrochloric acid for 2 h 30'. After evaporation of the solvent, an off-white solid was collected.

NMR ($D_2O$): 5.93 (d; 1H); 7.87 (d; 1H); 8.04 (s; 1H).

EXAMPLE 3

3-AMINO-5-METHYLPYRAZOLO[1,5-a]PYRIMIDIN-7-OL HYDROCHLORIDE

1st step: 3-NITRO-5-METHYLPYRAZOLO[1,5-a]PYRIMIDIN-7-OL

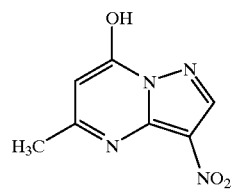

50 g of 4-nitro-2H-pyrazol-3-ylamine hydrochloride (prepared according to H. Dorn and H. Dilcher, Liebigs Ann. Chem., 707, 141, 1967) and 60 g of ethyl acetoacetate in 160 cc of acetic acid were introduced into a 500 cc three-necked round-bottomed flask equipped with a magnetic stirrer, a thermometer and a condenser. The reaction medium was refluxed for 12 h. The precipitate formed was filtered off at about 90° C. It was rinsed with diisopropyl ether and dried under vacuum over phosphorus pentoxide. 50 g of 3-nitro-5-methylpyrazolo[1,5-a]pyrimidin-7-ol were obtained in the form of yellow crystals. (Yield=84.5%; melting point=290° C. with decomposition).

NMR (DMSO-$d_6$): 2.42 (s, 3H); 6.03 (s, 1H); 8.61 (d, 1H); 12.69 (s, 1H);

ELEMENTAL ANALYSIS: $C_7H_6N_4O_3$ MW=194.15

|  | C | H | N | O |
|---|---|---|---|---|
| Calculated (%) | 43.31 | 3.12 | 28.86 | 24.72 |
| Found (%) | 43.12 | 3.11 | 28.77 | 24.65 |

2nd step: 3-AMINO-5-METHYLPYRAZOLO[1,5-a]PYRIMIDIN-7-OL HYDROCHLORIDE

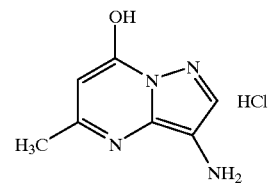

150 cc of acetic acid and 150 cc of water were introduced into a 1 litre autoclave, followed by 10 g of 3-nitro-5-methylpyrazolo[1,5-a]pyrimidin-7-ol and 1 g of 5% palladium-on-charcoal containing 50% water (Engelhard). 5 bar of hydrogen were introduced into the reactor, preheated to 30° C. After reacting for 1 h, the catalyst was filtered off through Celite. The filtrate was acidified with 100 cc of 7M hydrochloric acid solution. The hydrochloride precipitates out with stirring. It was filtered off and washed with diisopropyl ether. 4.2 g of 3-amino-5-methylpyrazolo[1,5-a]pyrimidin-7-ol hydrochloride were obtained in the form of white crystals. (Yield=41%).

NMR (DMSO-$d_6$): 2.37 (s, 3H); 5.71 (s, 1H); 8.00 (s, 1H); 10.32 (broad s, 3H); 13.09 (broad s, 1H);

ELEMENTAL ANALYSIS: $C_7H_8N_4O \cdot HCl$ MW=200.63

|  | C | H | N | O | Cl |
|---|---|---|---|---|---|
| Calculated (%) | 41.91 | 4.52 | 27.93 | 7.97 | 17.67 |
| Found (%) | 41.43 | 4.57 | 27.69 | 8.90 | 17.66 |

EXAMPLE 4

3-AMINO-7-β-HYDROXYETHYLAMINO-5-METHYLPYRAZOLO[1,5-a]PYRIMIDINE DIHYDROCHLORIDE

1st step: 7-CHLORO-5-METHYL-3-NITROPYRAZOLO[1,5-a]PYRIMIDINE

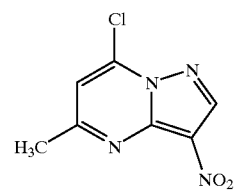

230 cc of phosphorus oxychloride, 15.4 g of N,N-dimethylaniline and 23.3 g of 3-amino-5-methylpyrazolo[1,5-a]pyrimidin-7-ol were introduced into a 500 cc three-necked flask equipped with a magnetic stirrer, a thermometer and a condenser. The reaction medium was refluxed for 2 h 30'. After evaporation of the phosphorus oxychloride under reduced pressure, a very viscous green oil was obtained, to which were added about 400 g of ice. A brown solid precipitated out. After stirring for 30 minutes, the precipitate was filtered off and rinsed with petroleum ether and then with diisopropyl ether. After drying under vacuum over phosphorus pentoxide, 21.4 g of 7-chloro-5-methyl-3-nitropyrazolo[1,5-a]pyrimidine were obtained in the form of a brown solid. (Yield=83.9%).

NMR (DMSO-d$_6$): 2.70 (s, 3H); 7.82 (s, 1H); 9.10 (s, 1H).

2nd step: 7-β-HYDROXYETHYLAMINO-5-METHYL-3-NITROPYRAZOLO[1,5-a]PYRIMIDINE

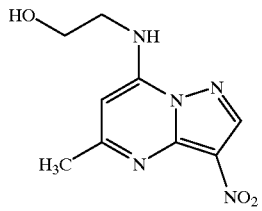

15 g of 7-chloro-5-methyl-3-nitropyrazolo[1,5-a]pyrimidine in 100 cc of ethanol were introduced into a 250 cc three-necked round-bottomed flask equipped with a magnetic stirrer, a thermometer and a condenser. 5 g of ethanolamine were added dropwise and the medium was refluxed for 30 minutes. After cooling to room temperature, the yellow precipitate was filtered off. This precipitate was rinsed with diisopropyl ether. After drying under vacuum over phosphorus pentoxide, 14.2 g of 7-β-hydroxyethylamino-5-methyl-3-nitropyrazolo[1,5-a]pyrimidine were obtained in the form of yellow crystals. (Yield=86%, melting point=231° C.).

NMR (DMSO-d$_6$): 2.52 (s, 3H); 3.52 (m, 2H); 3.66 (m, 2H); 4.96 (t, 1H); 6.64 (s, 1H); 8.48 (t, 1H); 8.89 (s, 1H);

ELEMENTAL ANALYSIS: $C_9H_{11}N_5O_3$ MW=237.22

|  | C | H | N | O |
|---|---|---|---|---|
| Calculated (%) | 45.57 | 4.67 | 29.52 | 20.23 |
| Found (%) | 45.09 | 4.59 | 29.40 | 20.63 |

3rd step: 3-AMINO-7-β-HYDROXYETHYLAMINO-5-METHYLPYRAZLO[1,5-a]PYRIMIDINE DIHYDROCHLORIDE

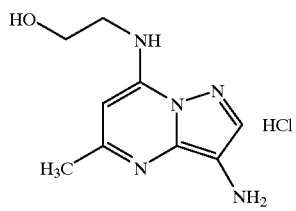

14 g of 7-β-hydroxyethylamino-5-methyl-3-nitropyrazolo[1,5-a]pyrimidine in 150 cc of acetic acid and 150 cc of water were introduced into a 500 cc autoclave, followed by 1 g of 5% palladium-on-charcoal containing 50% water (Engelhard). The reaction medium was preheated to 30° C. and an 8-bar pressure of hydrogen was introduced. The reaction started immediately and the temperature reached 60° C. At the end of the reaction, the catalyst was filtered off through Celite. The filtrate was acidified with 7M hydrochloric acid solution. The hydrochloride precipitated out with stirring. It was filtered off and washed with diisopropyl ether. 10 g of 3-amino-7-β-hydroxyethylamino-5-methylpyrazolo[1,5-a]pyrimidine dihydrochloride were obtained in the form of slightly grey crystals. (Yield=60%)

NMR (D$_2$O): 2.73 (s, 3H); 3.91 (m, 2H); 3.98 (m, 2H); 6.66 (s, 1H); 8.39 (s, 1H);

ELEMENTAL ANALYSIS: $C_9H_{13}N_5O \cdot 2$ HCl MW=280.16

|  | C | H | N | O | Cl |
|---|---|---|---|---|---|
| Calculated (%) | 38.59 | 5.4 | 25.05 | 5.71 | 25.31 |
| Found (%) | 38.52 | 5.32 | 24.59 | 6.42 | 25.15 |

EXAMPLE 5

2-METHYLPYRAZOLO[1,5-a]PYRIMIDINE-3,7-DIAMINE DIHYDROCHLORIDE

1st step: 2-METHYLPYRAZOLO[1,5-a]PYRIMIDIN-7-YLAMINE HYDROCHLORIDE

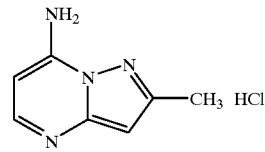

150 cc of 35% hydrochloric acid were introduced into a 500 cc three-necked flask equipped with a magnetic stirrer, a thermometer and a condenser, and 47.5 g of 3-amino-5-methylpyrazole dissolved in 100 cc of water were added dropwise. The temperature rose to 60° C. 47.5 g of 3-ethoxyacrylonitrile were then added and the reaction was refluxed for 1 h. The reaction medium was cooled and concentrated under reduced pressure. 50 cc of acetone were added and the precipitate obtained was filtered off. It was rinsed with diisopropyl ether. After drying under vacuum over phosphorus pentoxide, 78.7 g of 2-methylpyrazolo[1,5-a]pyrimidin-7-ylamine hydrochloride were obtained in the form of white crystals. (Yield=83%).

NMR (DMSO-d$_6$): 2.43 (s, 3H); 6.42 (s, 1H); 6.46 (d, 1H); 8.26 (d, 1H); 9.55 (broad s, 1H); 10.32 (broad s, 1H);

ELEMENTAL ANALYSIS: $C_7H_8N_4 \cdot HCl \cdot 0.5$ $H_2O$ MW=193.63

|  | C | H | N | O | Cl |
|---|---|---|---|---|---|
| Calculated (%) | 43.42 | 5.20 | 28.93 | 4.13 | 18.30 |
| Found (%) | 43.68 | 5.20 | 28.83 | 4.66 | 18.58 |

2nd step: 2-METHYL-3-NITROPYRAZOLO[1,5-a]PYRIMIDIN-7-YLAMINE

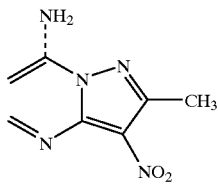

27 cc of 98% sulphuric acid were introduced into a 100 cc three-necked flask equipped with a magnetic stirrer, a thermometer and a condenser, after which 5.5 g of 2-methylpyrazolo[1,5-a]pyrimidin-7-ylamine hydrochloride were dissolved portionwise at 5° C. A mixture of 1.98 g of fuming nitric acid and 5 cc of 98% sulphuric acid was then added dropwise over 30 minutes. After reaction for 2 h 30', the medium was poured onto 200 cc of ice-cold water and neutralized with 122 g of 20% aqueous ammonia. The green precipitate which formed was filtered off. After drying under vacuum over phosphorus pentoxide, 3.8 g of 2-methyl-3-nitropyrazolo[1,5-a]pyrimidin-7-ylamine were obtained in the form of a green powder. (Crude yield=66%).

NMR (DMSO-$d_6$): 2.62 (s, 3H); 6.39 (d, 1H); 8.24 (d, 1H); 8.39 (broad s, 2H).

3rd step: 2-METHYLPYRAZOLO[1,5-a]PYRIMIDINE-3,7-DIAMINE DIHYDROCHLORIDE

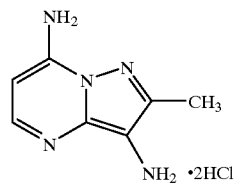

3.9 g of 2-methyl-3-nitropyrazolo[1,5-a]pyrimidin-7-ylamine in 150 cc of methanol were introduced into a 250 cc reactor, followed by 0.42 g of 5% palladium-on-charcoal containing 50% water (Engelhard). A 10-bar pressure of hydrogen was introduced into the reactor and the medium was brought to 90° C. After reaction for 40 minutes, the catalyst was filtered off through Celite and a stream of hydrogen chloride gas was passed through the filtrate. After stirring for 1 h, the precipitate was filtered off. It was washed with diisopropyl ether and dried under vacuum over phosphorus pentoxide. 2.2 g of 2-methylpyrazolo[1,5-a]pyrimidine-3,7-diamine dihydrochloride were obtained in the form of grey crystals. (Yield=46.5%).

NMR (DMSO-$d_6$): 2.60 (s, 3H); 6.50 (d, 1H); 8.45 (d, 1H); 9.98 (broad s, 2H); 10.88 (broad s, 4H);

ELEMENTAL ANALYSIS: $C_7H_9N_5 \cdot 2$ HCl MW=236.1

|  | C | H | N | Cl |
|---|---|---|---|---|
| Calculated (%) | 35.61 | 4.70 | 29.66 | 30.03 |
| Found (%) | 35.16 | 4.85 | 29.32 | 29.79 |
| Calculated with 0.16 mol of $H_2O$ | 35.18 | 4.77 | 29.30 | 29.66 |

APPLICATION EXAMPLES
EXAMPLES 1 TO 9 OF DYEING IN ALKALINE MEDIUM

The following dye compositions, in accordance with the invention, were prepared (contents in grams):

| COMPOSITION | 1 | 2 | 3 | 4 | 5 | 6 | 7 | 8 | 9 |
|---|---|---|---|---|---|---|---|---|---|
| Pyrazolo[1,5-a]pyrimidine-3,7-diamine dihydrochloride (base) | 0.66 | 0.66 | 0.66 | 0.66 | 0.66 | 0.66 | 0.66 | 0.66 | 0.66 |
| Resorcinol (coupler) | 0.33 | — | — | — | — | — | — | — | — |
| Meta-aminophenol (coupler) | — | 0.33 | — | — | — | — | — | — | — |
| 2-Methyl-5-hydroxyethylaminophenol (coupler) | — | — | 0.5 | — | — | — | — | — | — |
| 2-Methyl-5-aminophenol (coupler) | — | — | — | 0.37 | — | — | — | — | — |
| 2,4-Diaminophenoxyethanol dihydrochloride (coupler) | — | — | — | — | 0.72 | — | — | — | — |
| 2,6-Hydroxytoluene (coupler) | — | — | — | — | — | 0.37 | — | — | — |
| 6-Hydroxybenzomorpholine (coupler) | — | — | — | — | — | — | 0.45 | — | — |
| 6-Hydroxyindole (coupler) | — | — | — | — | — | — | — | 0.4 | — |
| 4-Hydroxyindole (coupler) | — | — | — | — | — | — | — | — | 0.4 |
| Common dye support 1 | (*) | (*) | (*) | (*) | (*) | (*) | (*) | (*) | (*) |

(*) Common dye support 1:

| 96° C. ethanol | 9.0 g |
|---|---|
| diethylenetriaminopentaacetic acid, pentasodium salt | 0.54 g |
| 35% sodium metabisulphite | 0.29 g |
| 20% aqueous ammnonia | 5.0 g |
| demineralized water qs | 50 g |

Each of the dye compositions 1 to 9 was mixed, at the time of use, with an amount of 50 g of 20-volumes hydrogen peroxide solution (6% by weight) whose pH was adjusted to approximately 2.5 with orthophosphoric acid.

Each resulting composition was applied immediately for 30 minutes to locks of natural grey hair containing 90% white hairs, or permanent-waved hair, at a rate of 10 g per 1 g of hair. The locks of hair were then rinsed, washed with a standard shampoo and then dried.

The locks of hair were dyed in the shades given in the table below:

| EXAMPLE | DYEING pH | COLORIMETRIC RESULT |
|---|---|---|
| 1 | 10 ± 0.2 | Coppery brown |
| 2 | 10 ± 0.2 | Iridescent red |
| 3 | 10 ± 0.2 | Iridescent copper |
| 4 | 10 ± 0.2 | Iridescent copper |
| 5 | 10 ± 0.2 | Iridescent plum |
| 6 | 10 ± 0.2 | Iridescent copper |
| 7 | 10 ± 0.2 | Iridescent red |
| 8 | 10 ± 0.2 | Ash-brown |
| 9 | 10 ± 0.2 | Plum |

EXAMPLES 10 to 18 OF DYEING IN ACIDIC MEDIUM

The following dye compositions, in accordance with the invention, were prepared (contents in grams):

| COMPOSITION | 10 | 11 | 12 | 13 | 14 | 15 | 16 | 17 | 18 |
|---|---|---|---|---|---|---|---|---|---|
| Pyrazolo[1,5-a]pyrimidine-3,7-diamine dihydrochloride (base) | 0.66 | 0.66 | 0.66 | 0.66 | 0.66 | 0.66 | 0.66 | 0.66 | 0.66 |
| Resorcinol (coupler) | 0.33 | — | — | — | — | — | — | — | — |
| Meta-aminophenol (coupler) | — | 0.33 | — | — | — | — | — | — | — |
| 2-Methyl-5-hydroxyethylaminophenol (coupler) | — | — | 0.5 | — | — | — | — | — | — |
| 2-Methyl-5-aminophenol (coupler) | — | — | — | 0.37 | — | — | — | — | — |
| 2,4-Diaminophenoxyethanol dihydrochloride (coupler) | — | — | — | — | 0.72 | — | — | — | — |
| 2,6-Hydroxytoluene (coupler) | — | — | — | — | — | 0.37 | — | — | — |
| 6-Hydroxybenzomorpholine (coupler) | — | — | — | — | — | — | 0.45 | — | — |
| 6-Hydroxyindole (coupler) | — | — | — | — | — | — | — | 0.4 | — |
| 4-Hydroxyindole (coupler) | — | — | — | — | — | — | — | — | 0.4 |
| Common dye support 2 | () | () | () | () | () | () | () | () | (**) |

(**) Common dye support 2:

| | |
|---|---|
| 96° C. ethanol | 9.0 g |
| diethylenetriaminopentaacetic acid, pentasodium salt | 0.54 g |
| 35% sodium metabisulphite | 0.29 g |
| $K_2HPO_4/KH_2PO_4$ (1.5M/0.5M) | 5.0 g |
| demineralized water qs | 50 g |

Each of the dye compositions 10 to 18 was mixed, at the time of use, with an amount of 50 g of 20-volumes hydrogen peroxide solution (6% by weight) whose pH was adjusted to approximately 2.5 with orthophosphoric acid.

Each resulting composition was applied immediately for 30 minutes to locks of natural grey hair containing 90% white hairs, or permanent-waved hair, at a rate of 10 g per 1 g of hair. The locks of hair were then rinsed, washed with a standard shampoo and then dried.

The locks of hair were dyed in the shades given in the table below:

| EXAMPLE | DYEING pH | COLORIMETRIC RESULT |
|---|---|---|
| 10 | 6.2 ± 0.2 | Coppery brown |
| 11 | 5.5 ± 0.2 | Iridescent red |
| 12 | 6 ± 0.2 | Iridescent copper |
| 13 | 6.1 ± 0.2 | Iridescent copper |
| 14 | 5.9 ± 0.2 | Iridescent plum |
| 15 | 5.3 ± 0.2 | Iridescent copper |
| 16 | 5.8 ± 0.2 | Iridescent red |
| 17 | 5.9 ± 0.2 | Ash-brown |
| 18 | 5.9 ± 0.2 | Plum |

EXAMPLES 19 to 21 OF DYEING IN ALKALINE MEDIUM

The following dye compositions, in accordance with the invention, were prepared (contents in grams):

| COMPOSITION | 19 | 20 | 21 |
|---|---|---|---|
| Pyrazolo [1,5-a]pyrimidine-3,7-diamine dihydrochloride (base) | 0.66 | 0.66 | — |
| 3-Amino-5-methylpyrazolo[1,5-a]pyrimidin-7-ol hydrochloride (base) | — | — | 0.796 |
| 3-Ureidoaniline dihydrochloride (coupler) | 0.67 | — | |
| 3-Ureido-1-dimethylaminobenzene | — | 0.54 | — |

-continued

| COMPOSITION | 19 | 20 | 21 |
|---|---|---|---|
| (coupler) | | | |
| 2,4-Diaminophenoxyethanol dihydrochloride | — | — | 0.72 |
| Common dye support 1 | (*) | (*) | (*) |

(*) Common dye support 1: This is identical to the one used in Examples 1 to 9 above.

The dyes were then prepared according to the process described above for Examples 1 to 9 above.

The locks of hair were dyed in the shades given in the table below:

| EXAMPLE | DYEING pH | COLORIMETRIC RESULTS |
|---|---|---|
| 19 | 10 ± 0.2 | Plum-blue |
| 20 | 10 ± 0.2 | Plum |
| 21 | 9.7 ± 0.2 | Aubergine |

EXAMPLES 22 TO 24 OF DYEING IN ACIDIC MEDIUM

The following dye compositions, in accordance with the invention, were prepared (contents in grams):

| COMPOSITION | 22 | 23 | 24 |
|---|---|---|---|
| Pyrazolo [1,5-a]pyrimidine-3,7-diamine dihydrochloride (base) | 0.66 | 0.66 | — |
| 3-Amino-5-methylpyrazolo[1,5-a]pyrimidin-7-ol hydrochloride (base) | — | — | 0.796 |
| 3-Ureidoaniline dihydrochloride (coupler) | 0.67 | — | — |
| 3-Ureido-1-dimethylaminobenzene (coupler) | — | 0.54 | — |
| 2,4-Diaminophenoxyethanol dihydrochloride | — | — | 0.72 |
| Common dye support 2 | () | () | (**) |

(**) Common dye support 2: This is identical to the one used in Examples 10 to 18 above.

The dyes were then prepared according to the process described previously for Examples 10 to 18 above.

The locks of hair were dyed in the shades given in the table below:

| EXAMPLE | DYEING pH | COLORIMETRIC RESULTS |
|---|---|---|
| 22 | 6 ± 0.2 | Plum-blue |
| 23 | 6.2 ± 0.2 | Plum |
| 24 | 5.3 ± 0.2 | Aubergine |

COMPARATIVE EXAMPLES 25 to 32

The following dye compositions, in accordance with the invention, were prepared (contents in grams):

| Compositions | 25 | 26 (*) | 27 | 28 (*) | 29 | 30 (*) | 31 | 32 (*) |
|---|---|---|---|---|---|---|---|---|
| Pyrazolo[1,5-a]pyrimidine-3,7-diamine dihydrochloride (base) | 0.66 | — | 0.66 | — | 0.66 | — | 0.66 | — |
| 4,5,6,7-Tetrahydropyrazolo[1,5-a]pyrimidin-3-ylamine trihydrochloride (base) | — | 0.74 | — | 0.74 | — | 0.74 | — | 0.74 |
| Resorcinol (coupler) | 0.33 | 0.33 | — | — | — | — | — | — |
| 2-Methyl-5-aminophenol (coupler) | — | — | 0.37 | 0.37 | — | — | — | — |
| 6-Hydroxybenzomorpholine (coupler) | — | — | — | — | 0.45 | 0.45 | — | — |
| 4-Hydroxyindole (coupler) | — | — | — | — | — | — | 0.40 | 0.40 |
| Common dye support 1 | (*) | (*) | (*) | (*) | (*) | (*) | (*) | (*) |

(*) Common dye support 1: This is identical to the one used in Examples 1 to 9 above.
(***): Examples not forming part of the invention.

The dyeing operations were then carried out on locks of natural grey hair containing 90% white hairs, according to the process described previously for Examples 1 to 9 above.

The colour of the locks was then evaluated in the Munsell system using a Minolta CM 2002 calorimeter.

The locks of hair thus dyed were then subjected to a test of fastness to shampooing (automatic machine).

To do this, the locks of hair were placed in a cup which was immersed in a solution of a standard shampoo at 37° C. The basket was subjected to an up-and-down motion of variable frequency and to a rotational motion, which reproduced the action of manual rubbing, thereby giving rise to the formation of a lather.

After a test time of 3 minutes, the locks were removed, rinsed and then dried. The dyed locks were subjected to 6 consecutive shampooing tests.

The colour of the locks was then evaluated again in the Munsell system using a Minolta CM 2002 calorimeter in order to determine the degradation of the colorations after these 6 shampoo washes.

According to the Munsell notation, a colour is defined by the expression H V/C in which the three parameters respectively denote the shade or Hue (H), the intensity or Value (V) and the purity or chromaticity (C), the oblique line in this expression simply being a convention and not indicating a ratio.

The difference in colour between two locks is calculated by applying the Nickerson formula: $\Delta E=0.4\ Co\Delta H+6\Delta V+3\Delta C$, as described for example in "Couleur, Industrie et Technique"; pages 14–17; vol. No. 5; 1978.

In this formula, $\Delta E$ represents the difference in colour between two locks, $\Delta H$, $\Delta V$ and $\Delta C$ represent the variation in absolute value of the parameters H, V and C, and Co represents the purity of the lock against which it is desired to evaluate the colour difference.

The results are given in the table below:

| EXAMPLE | Colour of the hair before shampooing | Colour of the hair after shampooing | $\Delta H$ | $\Delta V$ | $\Delta C$ | $\Delta E$ |
|---|---|---|---|---|---|---|
| 25 | 1.8 YR 3.2/3.7 | 1.4 YR 3.5/2.9 | 0.4 | 0.3 | 0.8 | 4.8 |
| 26(***) | 6.2 RP 3.1/4.7 | 7.1 RP 3.3/2.7 | 0.9 | 0.2 | 2.0 | 8.9 |
| 27 | 8.9 R 4.0/4.8 | 8.6 R 4.4/4.1 | 0.3 | 0.4 | 0.7 | 5.1 |
| 28(***) | 4.3 R 2.7/6.2 | 2.9 R 3.3/6.0 | 1.4 | 0.6 | 0.2 | 7.7 |
| 29 | 4.7 R 2 .8/4.8 | 3.6 R 3.2/4.6 | 1.1 | 0.4 | 0.2 | 5.1 |
| 30 (***) | 4.5 RP 2.4/3.1 | 3.5 RP 3.1/2.6 | 1.0 | 0.7 | 0.5 | 6.9 |
| 31 | 4.3 RP 2.6/3.9 | 3.7 RP 2.8/2.9 | 0.6 | 0.2 | 1.0 | 5.1 |
| 32 (***) | 8.4 P 2.0/4.4 | 7.4 P 2.6/5.1 | 1.0 | 0.6 | 0.7 | 7.5 |

(***): Examples not forming part of the invention

These results show that the compositions of Examples 25, 27, 29 and 31 in accordance with the invention, that is to say those containing pyrazolo[1,5-a]pyrimidine-3,7-diamine dihydrochloride as oxidation base, lead to a coloration which withstands shampooing much better than the compositions of Examples 26, 28, 30 and 32 not forming part of the invention, that is to say those containing 4,5,6,7-tetrahydropyrazolo[1,5-a]pyrimidin-3-ylamine trihydrochloride as oxidation base, as described, for example, in German application DE 4,133,957.

What is claimed is:

1. A composition comprising, in a medium suitable for dyeing, at least one oxidation base present in an amount effective for dyeing keratin fibers and ranging from 0.005 to 12 percent by weight relative to the total weight of said composition, and at least one coupler present in an amount ranging from 0.0001 to 10 percent by weight relative to the total weight of said composition, wherein said at least one oxidation base is a pyrazolo[1,5-a]pyrimidine compound of formula (I), an acid-addition salt thereof, a base-addition salt thereof, or a tautomeric form thereof, when a tautomeric equilibrium exists:

$$(X)_i\text{---}\begin{bmatrix}\text{structure}\end{bmatrix}\text{---}[NR_1R_2]_p \quad (I)$$
$$(OH)_n\text{---}\text{---}[NR_3R_4]_q$$

in which:

$R_1$, $R_2$, $R_3$ and $R_4$ each independently denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a ($C_1$–$C_4$)alkoxy($C_1$–$C_4$)alkyl radical, a $C_1$–$C_4$ aminoalkyl radical, wherein the amine may be protected with an acetyl, an amido or a sulphonyl, a ($C_1$–$C_4$)alkylamino($C_1$–$C_4$)alkyl radical, a di[($C_1$–$C_4$)alkyl]amino($C_1$–$C_4$)alkyl radical, wherein said dialkyls, together with the nitrogen atom to which they are attached, may form a 5- or a 6-membered aliphatic or heterocyclic ring, a hydroxy($C_1$–$C_4$)alkylamino ($C_1$–$C_4$)alkyl radical or a di[hydroxy($C_1$–$C_4$)alkyl]-amino($C_1$–$C_4$)alkyl radical;

the radicals X each independently denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$) alkylamino($C_1$–$C_4$)alkyl radical, a di[($C_1$–$C_4$)alkyl] amino($C_1$–$C_4$)alkyl radical, wherein said dialkyls, together with the nitrogen atom to which they are attached, may form a 5- or 6-membered aliphatic or heterocyclic ring, a hydroxy($C_1$–$C_4$)alkylamino-($C_1$–$C_4$)alkyl radical, a di[hydroxy($C_1$–$C_4$)alkyl]-amino($C_1$–$C_4$)alkyl radical, an amino radical, a ($C_1$–$C_4$)alkylamino radical or a di[($C_1$–$C_4$)alkyl]amino radical, a halogen atom, a carboxylic acid group or a sulphonic acid group;

i is equal to 0, 1, 2 or 3;

p is equal to 0 or 1;

q is equal to 0 or 1;

n is equal to 0 or 1;

with the proviso that:

(i) the sum p+q is not 0;

(ii) when p+q is equal to 2, then n is equal to 0 and the groups $NR_1R_2$ and $NR_3R_4$ occupy positions (2,3); (5,6); (6,7); (3,5) or (3,7);

(iii) and when p+q is equal to 1, then n is equal to 1 and the group $NR_1R_2$ or $NR_3R_4$ and the OH group occupy positions (2,3); (5,6); (6,7); (3,5) or (3,7); and further wherein said composition is an oxidation dye for keratin fibers.

2. A composition according to claim 1, wherein said keratin fibers are human hair.

3. A composition according to claim 1, wherein said pyrazolo[1,5-a]pyrimidine compound is:

pyrazolo[1,5-a]pyrimidine-3,7-diamine;

2-methylpyrazolo[1,5-a]pyrimidine-3,7-diamine;

2,5-dimethylpyrazolo[1,5-a]pyrimidine-3,7-diamine;

pyrazolo[1,5-a]pyrimidine-3,5-diamine;

2,7-dimethylpyrazolo[1,5-a]pyrimidine-3,5-diamine;

3-aminopyrazolo[1,5-a]pyrimidin-7-ol;

3-amino-5-methylpyrazolo[1,5-a]pyrimidin-7-ol;

3-aminopyrazolo[1,5-a]pyrimidin-5-ol;

2-(3-aminopyrazolo[1,5-a]pyrimidin-7-ylamino)ethanol;

3-amino-7-β-hydroxyethylamino-5-methylpyrazolo[1,5-a]pyrimidine;

2-(7-aminopyrazolo[1,5-a]pyrimidin-3-ylamino)ethanol;

2-[(3-aminopyrazolo[1,5-a]pyrimidin-7-yl)(2-hydroxyethyl)amino]ethanol;

2-[(7-aminopyrazolo[1,5-a]pyrimidin-3-yl)(2-hydroxyethyl)amino]ethanol;

5,6-dimethylpyrazolo[1,5-a]pyrimidine-3,7-diamine;

2,6-dimethylpyrazolo[1,5-a]pyrimidine-3,7-diamine; or 2,5-N-7, N-7-tetramethylpyrazolo[1,5-a]pyrimidine-3,7-diamine.

4. A composition according to claim 1, wherein said at least one oxidation base is present in a concentration ranging from 0.005 to 6% by weight relative to the total weight of said composition.

5. A composition according to claim 1, wherein said medium suitable for dyeing comprises water or a mixture of water and at least one organic solvent, wherein said at least one solvent is a $C_1$–$C_4$ lower alkanol, a glycerol, a glycol, a glycol ether, or an aromatic alcohol.

6. A composition according to claim 5, wherein said at least one organic solvent is present in a concentration ranging from 1 to 40% by weight relative to the total weight of said composition.

7. A composition according to claim 1, wherein said composition has a pH ranging from 3 to 12.

8. A composition according to claim 1, wherein said composition further comprises at least one direct dye.

9. A composition according to claim 1, wherein said at least one coupler is a meta-phenylenediamine, a meta-aminophenol, a meta-diphenol, heterocyclic coupler, or an addition salt thereof.

10. A composition according to claim 1, wherein said at least one coupler is present in a concentration ranging from 0.005 to 5% by weight relative to the total weight of said composition.

11. A composition according to claim 1, wherein said acid-addition salt is a hydrochloride, a hydrobromide, a sulphate, a tartrate, a lactate, or an acetate and said base-addition salt is a salt obtained with sodium hydroxide, potassium hydroxide, aqueous ammonia or an amine.

12. A composition according to claim 1, wherein said composition is in the form of a liquid, a cream, a gel, or any form suitable for dyeing keratin fibers.

13. A process for dyeing keratin fibers comprising applying an effective amount of at least one composition according to claim 1 to said keratin fibers and developing a desired coloration by exposing the composition according to claim 1 to air or an oxidizing agent, optionally in the presence of oxidation catalysts.

14. A process according to claim 13, wherein said keratin fibers are human hair.

15. A process according to claim 13, wherein said desired coloration is developed in air by contact with atmospheric oxygen.

16. A process according to claim 13, wherein said desired coloration is developed by either:
  adding said oxidizing agent to said at least one composition and then applying to said keratin fibers; or
  simultaneously or sequentially applying said at least one composition and an oxidizing composition containing said oxidizing agent to said keratin fibers.

17. A process according to claim 16, wherein said oxidizing agent is hydrogen peroxide, urea peroxide, an alkali metal bromate or a persalt.

18. A process according to claim 17, wherein said persalt is a perborate or a persulphate.

19. A process according to claim 17, wherein said oxidizing agent is hydrogen peroxide.

20. A process according to claim 16, wherein:
  said oxidizing composition comprising at least one oxidizing agent is added to said at least one composition in an amount sufficient to develop a coloration, wherein a mixture is obtained;
  said resulting mixture is applied to said keratin fibers and left on said keratin fibers for a time ranging from 3 to 50 minutes;
  said keratin fibers are rinsed;
  said keratin fibers are washed with shampoo;
  said keratin fibers are rinsed again; and
  said keratin fibers are dried.

21. A process according to claim 20, wherein said mixture is left on said keratin fibers for a time ranging from 5 to 30 minutes.

22. A multi-compartment device or multi-compartment dyeing kit comprising:
  a first compartment containing at least one composition according to claim 1, and
  a second compartment containing at least one oxidizing composition.

23. A composition comprising, in a medium suitable for dyeing at least one oxidation base and at least one additional oxidation base,
  wherein said at least one oxidation base is a pyrazolo[1,5-a]pyrimidine compound of formula (I), an acid-addition salt thereof, a base-addition salt thereof, or a tautomeric form thereof, when a tautomeric equilibrium exists:

$$(I)$$

$$(X)_i \text{—} \underset{(OH)_n}{\underset{|}{\bigg[}} \text{pyrazolo[1,5-a]pyrimidine} \bigg] \text{—} [NR_1R_2]_p, [NR_3R_4]_q$$

in which:
  $R_1$, $R_2$, $R_3$ and $R_4$ each independently denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a ($C_1$–$C_4$)alkoxy($C_1$–$C_4$)alkyl radical, a $C_1$–$C_4$ aminoalkyl radical, wherein the amine may be protected with an acetyl, an amido or a sulphonyl, a ($C_1$–$C_4$)alkylamino($C_1$–$C_4$)alkyl radical, a di[($C_1$–$C_4$)alkyl]amino($C_1$–$C_4$)alkyl radical, wherein said dialkyls, together with the nitrogen atom to which they are attached, may form a 5- or a 6-membered aliphatic or heterocyclic ring, a hydroxy($C_1$–$C_4$)alkylamino ($C_1$–$C_4$)alkyl radical or a di[hydroxy($C_1$–$C_4$)alkyl]-amino($C_1$–$C_4$)alkyl radical;
  the radicals X each independently denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$) alkylamino($C_1$–$C_4$)alkyl radical, a di[($C_1$–$C_4$)alkyl] amino($C_1$–$C_4$)alkyl radical, wherein said dialkyls, together with the nitrogen atom to which they are attached, may form a 5- or 6-membered aliphatic or heterocyclic ring, a hydroxy($C_1$–$C_4$)alkylamino-($C_1$–$C_4$)alkyl radical, a di[hydroxy($C_1$–$C_4$)alkyl]-amino($C_1$–$C_4$)alkyl radical, an amino radical, a ($C_1$–$C_4$)alkylamino radical or a di[($C_1$–$C_4$)alkyl]amino radical, a halogen atom, a carboxylic acid group or a sulphonic acid group;
  i is equal to 0, 1, 2 or 3;
  p is equal to 0 or 1;

q is equal to 0 or 1;

n is equal to 0 or 1;

with the proviso that:
(i) the sum p+q is not 0;
(ii) when p+q is equal to 2, then n is equal to 0 and the groups $NR_1R_2$ and $NR_3R_4$ occupy positions (2,3); (5,6); (6,7); (3,5) or (3,7);
(iii) and when p+q is equal to 1, then n is equal to 1 and the group $NR_1R_2$ or $NR_3R_4$ and the OH group occupy positions (2,3); (5,6); (6,7); (3,5) or (3,7); wherein said at least one additional oxidation base is different than said at least one oxidation base of formula (I); and further wherein said composition is an oxidation dye for keratin fibers.

24. A composition according to claim 23, wherein said at least one additional oxidation base is present in a concentration ranging from 0.0005 to 12% by weight relative to the total weight of said composition.

25. A composition according to claim 24, wherein said at least one additional oxidation base is present in a concentration ranging from 0.005 to 6% by weight relative to the total weight of said composition.

26. A composition according to claim 23, wherein said at least one additional oxidation base is a para-phenylenediamine, a bis(phenyl)alkylenediamine, a para-aminophenol, an ortho-aminophenol or a heterocyclic base, wherein said at least one additional oxidation base is different from said at least one oxidation base, said at least one oxidation base is a pyrazolo[1,5-a]pyrimidine compound of formula (I), an acid-addition salt thereof, a base-addition salt thereof, or a tautomeric form thereof, when a tautomeric equilibrium exists:

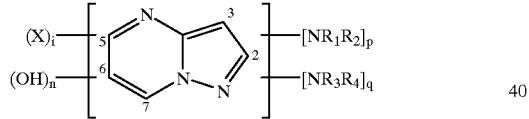

(I)

in which:
$R_1$, $R_2$, $R_3$ and $R_4$ each independently denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a ($C_1$–$C_4$)alkoxy($C_1$–$C_4$)alkyl radical, a $C_1$–$C_4$ aminoalkyl radical, wherein the amine may be protected with an acetyl, an amido or a sulphonyl, a ($C_1$–$C_4$)alkylamino($C_1$–$C_4$)alkyl radical, a di[($C_1$–$C_4$)alkyl]amino($C_1$–$C_4$)alkyl radical, wherein said dialkyls, together with the nitrogen atom to which they are attached, may form a 5- or a 6-membered aliphatic or heterocyclic ring, a hydroxy($C_1$–$C_4$)alkylamino ($C_1$–$C_4$)alkyl radical or a di[hydroxy($C_1$–$C_4$)alkyl]-amino($C_1$–$C_4$)alkyl radical;

the radicals X each independently denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$)alkylamino($C_1$–$C_4$)alkyl radical, a di[($C_1$–$C_4$) alkyl]amino($C_1$–$C_4$)alkyl radical, wherein said dialkyls, together with the nitrogen atom to which they are attached, may form a 5- or 6-membered aliphatic or heterocyclic ring, a hydroxy($C_1$–$C_4$)alkylamino-($C_1$–$C_4$)alkyl radical, a di[hydroxy($C_1$–$C_4$)alkyl]-amino($C_1$–$C_4$)alkyl radical, an amino radical, a ($C_1$–$C_4$)alkylamino radical or a di[($C_1$–$C_4$)alkyl]amino radical, a halogen atom, a carboxylic acid group or a sulphonic acid group;

i is equal to 0, 1, 2 or 3;

p is equal to 0 or 1;

q is equal to 0 or 1;

n is equal to 0 or 1;

with the proviso that:
(i) the sum p+q is not 0;
(ii) when p+q is equal to 2, then n is equal to 0 and the groups $NR_1R_2$ and $NR_3R_4$ occupy positions (2,3); (5,6); (6,7); (3,5) or (3,7);
(iii) and when p+q is equal to 1, then n is equal to 1 and the group $NR_1R_2$ or $NR_3R_4$ and the OH group occupy positions (2,3); (5,6); (6,7); (3,5) or (3,7).

* * * * *